(12) United States Patent
Wei et al.

(10) Patent No.: US 10,853,135 B2
(45) Date of Patent: Dec. 1, 2020

(54) RESOURCE ALLOCATION METHOD AND APPARATUS FOR GENE ANALYSIS

(71) Applicant: HUAWEI TECHNOLOGIES CO., LTD., Shenzhen, Guangdong (CN)

(72) Inventors: Jiansheng Wei, Shenzhen (CN); Guowei Huang, Shenzhen (CN); Liqun Deng, Shenzhen (CN)

(73) Assignee: Huawei Technologies Co., Ltd., Guangdong (CN)

( * ) Notice: Subject to any disclaimer, the term of this patent is extended or adjusted under 35 U.S.C. 154(b) by 117 days.

(21) Appl. No.: 16/153,099

(22) Filed: Oct. 5, 2018

(65) Prior Publication Data

US 2019/0042311 A1 Feb. 7, 2019

Related U.S. Application Data

(63) Continuation of application No. PCT/CN2017/079306, filed on Apr. 1, 2017.

(30) Foreign Application Priority Data

Apr. 8, 2016 (CN) .......................... 2016 1 0219164

(51) Int. Cl.
*G06F 9/50* (2006.01)
*G16B 50/30* (2019.01)
(Continued)

(52) U.S. Cl.
CPC ............... *G06F 9/50* (2013.01); *G16B 20/00* (2019.02); *G16B 50/30* (2019.02); *G06F 9/52* (2013.01); *G16B 30/10* (2019.02)

(58) Field of Classification Search
CPC ......... G06F 9/50; G06F 9/5027; G06F 9/5011
See application file for complete search history.

(56) References Cited

U.S. PATENT DOCUMENTS

2004/0234995 A1 11/2004 Musick et al.
2013/0332081 A1* 12/2013 Reese .................... G16B 20/00
702/19

(Continued)

FOREIGN PATENT DOCUMENTS

CN 101118611 A 2/2008
CN 101608233 A 12/2009
(Continued)

OTHER PUBLICATIONS

Kathiresan et al., "Optimization of Data-Intensive Next Generation Sequencing in High Performance Computing" (Year: 2015).*
(Continued)

*Primary Examiner* — Phillip H Nguyen
(74) *Attorney, Agent, or Firm* — Fish & Richardson P.C.

(57) ABSTRACT

The present disclosure relates to a resource allocation method for gene analysis. In one example method, a parameter value that is of the target chromosome region and that is used for resource allocation is obtained according to a sequenced read in a target chromosome region. A computing resource is allocated, according to the parameter value that is of the target chromosome region and that is used for resource allocation, to an operation in a cleansing and variant calling task that is in the gene analysis and that is performed on the sequenced read in the target chromosome region.

22 Claims, 4 Drawing Sheets

(51) Int. Cl.
*G16B 20/00* (2019.01)
*G16B 30/10* (2019.01)
*G06F 9/52* (2006.01)

(56) References Cited

U.S. PATENT DOCUMENTS

| | | | | |
|---|---|---|---|---|
| 2014/0214333 | A1* | 7/2014 | Plattner | G16B 50/00 702/19 |
| 2016/0048633 | A1* | 2/2016 | Pham | G06F 16/9024 707/737 |
| 2016/0081081 | A1 | 3/2016 | Xu et al. | |
| 2016/0125130 | A1* | 5/2016 | Le Cocq | G16B 30/00 506/9 |
| 2016/0239681 | A1* | 8/2016 | Plattner | G06F 16/256 |
| 2017/0169160 | A1* | 6/2017 | Hu | G16B 30/00 |
| 2019/0156916 | A1* | 5/2019 | Deng | G06F 40/205 |

FOREIGN PATENT DOCUMENTS

| | | |
|---|---|---|
| CN | 101865843 A | 10/2010 |
| CN | 101930502 A | 12/2010 |
| CN | 104244426 A | 12/2014 |
| CN | 105046109 A | 11/2015 |
| CN | 105117619 A | 12/2015 |
| WO | 03042780 A3 | 8/2003 |

OTHER PUBLICATIONS

Shringarpure et al., "Inexpensive and Highly Reproducible Cloud-Based Variant Calling of 2,535 Human Genomes" (Year: 2015).*

Puckelwartz et al., "Supercomputing for the parallelization of whole genome analysis" (Year: 2014).*

Cheng et al., "Assessing single nucleotide variant detection and genotype calling on whole-genome sequenced individuals" (Year: 2014).*

Yang et al., "SAMSVM: A tool for misalignment ⁻Itration of SAM-format sequences with support vector machine" (Year: 2015).*

Folarin et al., "NGSeasy: a next generation sequencing pipeline in Docker containers [version 1; peer review: 3 approved with reservations]" (Year: 2015).*

Office Action issued in Chinese Application No. 201610219164.2 dated Feb. 3, 2020, 12 pages (With English Translation).

Mushtaq Hamid et al: "Cluster-based Apache Spark implementation of the GATK DNA analysis pipeline", 2015 IEEE International Conference on Bioinformatics and Biomedicine (BIBM), Nov. 2015. 7 pages, XP032833721.

Benjamin J Kelly et al: "Churchill: an ultra-fast, deterministic, highly scalable and balanced parallelization strategy for the discovery of human genetic variation in clinical and population-scale genomics", Genome Biology, vol. 16, No. 1, Jan. 1, 2015. 14 pages, XP055560791.

Aggour Kareem S et al: "A highly parallel nextgeneration DNA sequencing data analysis pipeline in Hadoop", 2015 IEEE International Conference on Bioinformatics and Biomedicine (BIBM), Nov. 2015. pp. 756-763, XP032833608.

Yongchul Kwon et al: "SkewTune: Mitigating Skew in MapReduce Applications", Proceedings of the 2012 ACM SIGMOD International Conference on Management of Data, May 2012. p. 25-36, XP055159601.

Extended European Search Reports issued in European Application No. 17778632.4 dated Mar. 6, 2019, 11 pages.

Dries Decap et al, Halvade: scalable sequence analysis with MapReduce. Bioinformatics, 2015, pp. 1-7.

International Search Report and Written Opinion issued in International Application No. PCT/CN2017/079306 dated Jul. 5, 2017, 15 pages.

* cited by examiner

200

| 210 |
| --- |
| Obtain, according to a sequenced read in a target chromosome region, a parameter value that is of the target chromosome region and that is used for resource allocation |

| 220 |
| --- |
| Allocate, according to the parameter value that is of the target chromosome region and that is used for resource allocation, a computing resource to an operation in a cleansing and variant calling task that is in gene analysis and that is performed on the sequenced read in the target chromosome region |

FIG. 2

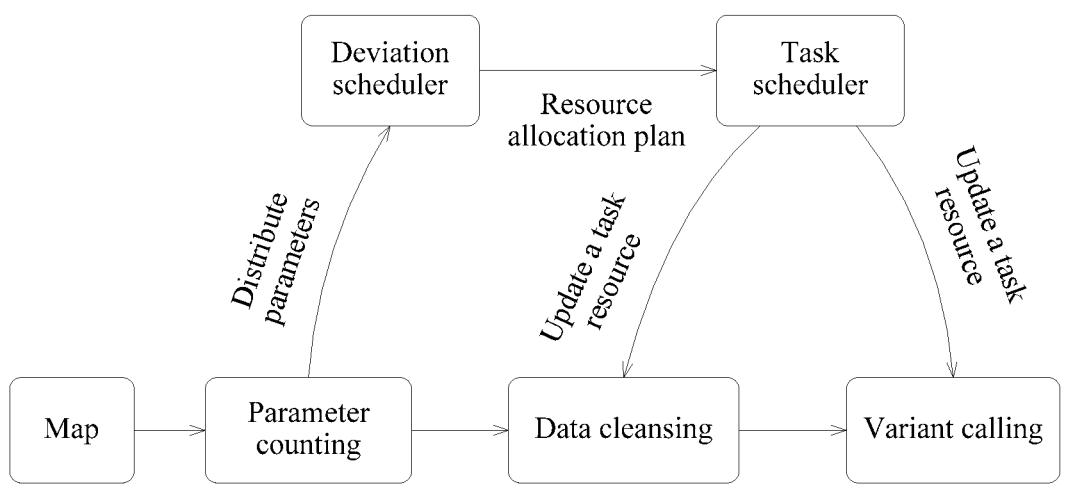

FIG. 3

RESOURCE ALLOCATION METHOD AND APPARATUS FOR GENE ANALYSIS

CROSS-REFERENCE TO RELATED APPLICATIONS

This application is a continuation of International Application No. PCT/CN2017/079306, filed on Apr. 1, 2017, which claims priority to Chinese Patent Application No. 201610219164.2, filed on Apr. 8, 2016. The disclosures of the aforementioned applications are hereby incorporated by reference in their entireties.

TECHNICAL FIELD

Embodiments of this application relate to the field of computers, to a resource allocation method and apparatus for gene analysis.

BACKGROUND

With advancement of deoxyribonucleic acid (Deoxyribonucleic Acid, DNA) sequencing technologies, gene analysis has become an important means for detection and targeted treatment of hereditary and mutation diseases.

A gene is a DNA sequence that carries hereditary information. A DNA is a long-chain polymer, and composition units include four types of deoxyribonucleotides. A carrier of the DNA may be referred to as a chromosome.

In short, gene analysis includes the following three stages: DNA sequencing (Sequencing), DNA sequence assembly (Assembly) and variant calling (Variant Calling), and gene annotation (Annotation) and analysis.

In the DNA sequencing, a DNA is divided into multiple segments, and then a sequencer simultaneously sequences dozens to millions of segments. A base symbol sequence that is output after sequencing may be referred to as a base sequence read.

The DNA sequence assembly and variant calling is a process in which base sequence reads (Read) that are output by the sequencer are assembled into a DNA sequence by using a computer method, and a variant base locus is found by comparing the DNA sequence with a reference DNA. The base sequence reads that are output by the sequencer are mapped, to determine coordinates of each read. A read with known coordinates after mapping processing is referred to as a sequenced read. Then, each chromosome region may be used as an object, so as to perform cleansing and variant calling on a sequenced read in each chromosome region; and variant calling results of the chromosome regions are combined.

A cleansing and variant calling task in a chromosome region requires a large quantity of computing resources. Therefore, a proper resource allocation method is urgently needed, so as to improve the computing resource utilization efficiency and the gene analysis execution efficiency.

SUMMARY

Embodiments of this application provide a resource allocation method and apparatus for a gene analysis operation, to efficiently use a computing resource.

According to a first aspect, a resource allocation method for gene analysis is provided. The method includes: obtaining, according to a sequenced read in a target chromosome region, a parameter value that is of the target chromosome region and that is used for resource allocation; and allocating, according to the parameter value that is of the target chromosome region and that is used for resource allocation, a computing resource to an operation in a cleansing and variant calling task that is in the gene analysis and that is performed on the sequenced read in the target chromosome region.

In an embodiment of this application, a parameter value used for resource allocation is obtained according to a sequenced read in a chromosome region, and a computing resource is allocated to an operation in a cleansing and variant calling task for the sequenced read according to the parameter value. Therefore, the computing resource can be dynamically scheduled according to the sequenced read in the chromosome region, so that the resource can be efficiently used.

With reference to the first aspect, in a first possible implementation of the first aspect, a parameter that is of the target chromosome region and that is used for resource allocation includes: at least one of a quantity of sequenced reads in the target chromosome region or an average coverage depth of loci in the target chromosome region.

A quantity of sequenced reads in a chromosome region is a quantity of sequenced reads that cover the chromosome region. An average coverage depth value of loci in the chromosome region may be calculated in the following manner: A sum of length values of all sequenced reads that cover the chromosome region is calculated, the sum of the length values of all the sequenced reads that cover the chromosome region is divided by a length value of the chromosome region, and a quotient value is used as the average coverage depth value of the loci in the chromosome region.

In an embodiment of this application, a location of a base in a DNA is referred to as a locus. A sequenced read is a read that has definite chromosome coordinates after undergoing mapping processing.

With reference to either the first aspect or the foregoing possible implementation of the first aspect, in a second possible implementation of the first aspect, the obtaining, according to a sequenced read in a target chromosome region, a parameter value that is of the target chromosome region and that is used for resource allocation includes: obtaining a coverage depth value of a locus in the target chromosome region according to a quantity value of sequenced reads that cover the locus in the target chromosome region; determining a gap in the target chromosome region according to the coverage depth value of the locus in the target chromosome region, to obtain at least two segments in the target chromosome region that use the gap as an interval, where a coverage depth value of a locus in the gap is less than a first threshold, the gap is a segment or a locus in the target chromosome region, and the at least two segments do not include the gap; determining some or all of the at least two segments in the target chromosome region as a target segment; using at least one of a quantity of target segments, a length of the target segment, a quantity of sequenced reads in the target segment, or a coverage depth of the target segment as a parameter that is of the target chromosome region and that is used for resource allocation, where the coverage depth of the target segment is an average coverage depth of loci in the target segment; and obtaining the parameter value that is of the target chromosome region and that is used for resource allocation.

The quantity of sequenced reads in the target segment is a quantity of sequenced reads that cover the target segment. The length of the target segment may be a quantity of loci in the target segment. The average coverage depth value of the loci in the target segment may be calculated in the following manner: A sum of length values of the sequenced reads in the target segment is calculated, the sum of length values of the sequenced reads in the target segment is divided by a length value of the target segment, and a quotient value is used as the average coverage depth value of the loci in the target segment.

With reference to any one of the first aspect or the foregoing possible implementations of the first aspect, in a third possible implementation of the first aspect, the obtaining, according to a sequenced read in a target chromosome region, a parameter value that is of the target chromosome region and that is used for resource allocation includes: obtaining a coverage depth value of a locus in the target chromosome region according to a quantity value of sequenced reads that cover the locus in the target chromosome region; determining a gap in the target chromosome region according to the coverage depth value of the locus in the target chromosome region, to obtain at least two segments in the target chromosome region that use the gap as an interval, where a coverage depth value of a locus in the gap is less than a first threshold, the gap is a segment or a locus in the target chromosome region, and the at least two segments do not include the gap; determining some or all of the at least two segments in the target chromosome region as a target segment, where there are at least two target segments; using a weighted average value of coverage depth values of the target segments as a parameter that is of the target chromosome region and that is used for resource allocation, where the coverage depth of the target segment is an average coverage depth of loci in the target segment; and obtaining the parameter value that is of the target chromosome region and that is used for resource allocation.

With reference to the third possible implementation of the first aspect, in a fourth possible implementation of the first aspect, the obtaining the parameter value that is of the target chromosome region and that is used for resource allocation includes: calculating the weighted average value of the coverage depth values of the target segments by using a ratio of a length value of a target segment of the target segments to a length value of the target chromosome region as a weight value of a coverage depth value of the target segment.

It should be understood that the target segment herein may be any target segment in the target chromosome region, that is, for any target segment, a ratio of a length value of the target segment to the length value of the target chromosome region may be used as a weight value of a coverage depth value of the target segment.

With reference to any one of the second to the fourth implementations of the first aspect, in a fifth possible implementation of the first aspect, the determining some or all of the at least two segments in the target chromosome region as a target segment includes: using, as the target segment, at least one of a segment that is in the at least two segments in the target chromosome region and in which a quantity of sequenced reads meets a preset quantity requirement or a segment that is in the at least two segments in the target chromosome region and in which an average coverage depth of loci meets a preset coverage depth requirement.

For example, each of k segments that are in the at least two segments and that have a maximum average coverage depth of loci is determined as the target segment, or each segment that is in the at least two segments and in which an average coverage depth of loci is greater than a second threshold is determined as the target segment, or each of k segments that are in the at least two segments and have a maximum quantity of sequenced reads is determined as the target segment, or each segment that is in the multiple segments and in which a quantity of sequenced reads is greater than a third threshold is determined as the target segment.

Therefore, in an embodiment of this application, a gap in which an average coverage depth of loci is less than a threshold is used as an interval, to divide the chromosome region into multiple segments, and the target segment is selected from the multiple segments. A parameter of the target segment is used as the parameter used for resource allocation, and a segment that has a relatively large quantity of reads or a relatively large coverage depth may be locally counted, to better determine a deviation status of the parameter that is in the target chromosome region and that is used for resource allocation. In addition, the segment that is in the multiple segments and has a relatively large coverage depth or a relatively large quantity of reads is further selected as the target segment, so that parameters referenced during resource allocation are more meaningful.

With reference to any one of the first aspect or the foregoing possible implementations of the first aspect, in a sixth possible implementation of the first aspect, the allocating, according to the parameter value that is of the target chromosome region and that is used for resource allocation, a computing resource to an operation in a cleansing and variant calling task that is in the gene analysis and that is performed on the sequenced read in the target chromosome region includes: obtaining an average value of respective parameter values that are of at least two chromosome regions and that are used for resource allocation; obtaining, according to the parameter value that is of the target chromosome region and that is used for resource allocation and the average value of the respective parameter values that are of the at least two chromosome regions and that are used for resource allocation, a deviation of the parameter value that is of the target chromosome region and that is used for resource allocation from the average value of the respective parameter values that are of the at least two chromosome regions and that are used for resource allocation; and allocating the computing resource to the operation according to the deviation.

With reference to the sixth possible implementation of the first aspect, in a seventh possible implementation of the first aspect, the at least two chromosome regions include the target chromosome region.

With reference to the sixth or the seventh possible implementation of the first aspect, in an eighth possible implementation of the first aspect, the deviation includes a ratio of the weighted average value of the coverage depth values of the target segments to a weighted average value of respective coverage depth values of the at least two chromosome regions; and the coverage depth of the chromosome region includes a weighted average value of respective coverage depth values of loci in at least two segments in the chromosome region, or includes an average coverage depth of loci in the chromosome region.

With reference to the sixth or the seventh possible implementation of the first aspect, in a ninth possible implementation of the first aspect, the deviation includes a ratio of the quantity value of the sequenced reads in the target chromosome region to an arithmetic average value of respective quantity values of sequenced reads in the at least two chromosome regions.

It should be understood that in an embodiment of this application, alternatively, the deviation may be determined according to a difference between the parameter value that is of the target chromosome region and that is used for resource allocation and the average value of the respective parameter values that are of the at least two chromosome regions and that are used for resource allocation, or may be determined in another manner provided that a degree of the deviation of the parameter value that is of the target chromosome region and that is used for resource allocation from the average value of the respective parameter values that are of the at least two chromosome regions and that are used for resource allocation can be reflected.

It should be further understood that in addition to allocating the resource according to the deviation of the parameter value that is of the target chromosome region and that is used for resource allocation from the average value of the respective parameter values that are of the at least two chromosome regions and that are used for resource allocation, the computing resource may be allocated in another manner. For example, the resource is allocated according to the parameter value that is of the target chromosome region and that is used for resource allocation, and the average value of the respective parameter values that are of the at least two chromosome regions and that are used for resource allocation is not considered.

It should be further understood that, in an embodiment of this application, multiple parameters may be considered during resource allocation.

With reference to any one of the sixth to the ninth possible implementations of the first aspect, in a tenth possible implementation of the first aspect, the allocating the computing resource to the operation according to the deviation includes: adjusting, according to the deviation, an initial computing resource used for implementing the operation, to obtain the computing resource.

In an embodiment of this application, during resource allocation, if a task requires relatively more computing resources, some of resources that are pre-allocated to a task that requires a relatively small computing amount may be reallocated to the task that requires relatively more computing resources. Alternatively, computing resources pre-allocated to a task that requires relatively fewer computing resources may not change, but instead, another computing resource (a spare computing resource that has not been pre-allocated) is allocated to a task that requires relatively more computing resources.

Optionally, in an embodiment of this application, when there is a pre-configured computing resource, a resource allocation plan may be updated in the following calculation manner:

$R$-update=$R$+[$t \times$($x$-region/$x$-average$-1$)$\times P$]=<$r$-cpu_cores+[$t \times$($x$-region/$x$-average$-1$)$\times p$-cpu_cores], $r$-mem+[$t \times$($x$-region/$x$-average$-1$)$\times p$-mem], $r$-gpu+[$t \times$($x$-region/$x$-average$-1$)$\times p$-gpu], $r$-fpga+[$t \times$($x$-region/$x$-average$-1$)$\times p$-fpga]>, where x-region is the parameter value that is of the target chromosome region and that is used for resource allocation; x-average is the average value of the parameter values that are of the at least two chromosome regions and that are used for resource allocation; R<r-cpu_cores, r-mem, r-gpu, r-fpga> is a basic resource allocation plan of one or more operations in the cleansing and variant calling task for the sequenced read, and r-cpu_cores, r-mem, r-gpu, and r-fpga are respectively used to describe a CPU core resource, a memory resource, a GPU resource, and an FPGA resource that are pre-allocated and required for performing the one or more operations; P<p-cpu_cores, p-mem, p-gpu, p-fpga> describes a resource allocation adjustment unit of the one or more operations; t is an adjustment parameter; and [ ] is a rounding operator.

Therefore, in an embodiment of this application, a difference between computing amounts of chromosome region analysis tasks is determined according to sequenced reads in chromosome regions, and guidance is provided for a scheduling system so that the scheduling system preferentially allocates an advantaged computing resource to a complex analysis task, so as to improve overall performance of a gene analysis operation, improve use efficiency of computing resources in an analysis system, and generally reduce time overheads of the gene analysis operation.

With reference to any one of the first aspect or the foregoing possible implementations of the first aspect, in an eleventh possible implementation of the first aspect, the at least one operation includes at least one of a deduplication operation, a filtering operation, a local realignment operation, a base quality score recalibration operation, or a variant calling operation.

Optionally, the deduplication operation, the filtering operation, the local realignment operation, and the base quality score recalibration operation are in a relatively strong correlation with the quantity of sequenced reads in the target chromosome region. Therefore, before each of the deduplication operation, the filtering operation, the local realignment operation, and the base quality score recalibration operation, a resource is allocated according to a quantity of sequenced reads that are in a chromosome region and that undergo previous processing, or a resource is allocated according to a quantity of sequenced reads in a chromosome region only before the deduplication operation.

Optionally, the variant calling operation is in a relatively strong correlation with the weighted average value of the coverage depth values of the target segments. Therefore, the target segments and the weighted average value of the coverage depth values of the target segments may be determined before the variant calling operation according to a quantity of sequenced reads that are in the chromosome region and that undergo previous processing, and a resource is allocated.

With reference to any one of the first aspect or the foregoing possible implementations of the first aspect, in a twelfth possible implementation of the first aspect, the computing resource includes at least one of a central processing unit resource, a memory resource, an image processing unit resource, or a field programmable gate array resource.

According to a second aspect, a resource allocation apparatus for gene analysis is provided, and the apparatus includes: an obtaining unit, configured to obtain, according to a sequenced read in a target chromosome region, a parameter value that is of the target chromosome region and that is used for resource allocation; and an allocation unit, configured to allocate, according to the parameter value that is of the target chromosome region and that is used for resource allocation, a computing resource to an operation in a cleansing and variant calling task that is in the gene analysis and that is performed on the sequenced read in the target chromosome region.

With reference to the second aspect, in a first possible implementation of the second aspect, a parameter that is of the target chromosome region and that is used for resource allocation includes: at least one of a quantity of sequenced reads in the target chromosome region or an average coverage depth of loci in the target chromosome region.

With reference to the second aspect, in a second possible implementation of the second aspect, the obtaining unit is configured to: obtain a coverage depth value of a locus in the target chromosome region according to a quantity value of sequenced reads that cover the locus in the target chromosome region; determine a gap in the target chromosome region according to the coverage depth value of the locus in the target chromosome region, to obtain at least two segments in the target chromosome region that use the gap as an interval, where a coverage depth value of a locus in the gap is less than a first threshold, the gap is a segment or a locus in the target chromosome region, and the at least two segments do not include the gap; determine some or all of the at least two segments in the target chromosome region as a target segment; use at least one of a quantity of target segments, a length of the target segment, a quantity of sequenced reads in the target segment, or a coverage depth of the target segment as a parameter that is of the target chromosome region and that is used for resource allocation, where the coverage depth of the target segment is an average coverage depth of loci in the target segment; and obtain the parameter value that is of the target chromosome region and that is used for resource allocation.

With reference to the second aspect, in a third possible implementation of the second aspect, the obtaining unit is configured to: obtain a coverage depth value of a locus in the target chromosome region according to a quantity value of sequenced reads that cover the locus in the target chromosome region; determine a gap in the target chromosome region according to the coverage depth value of the locus in the target chromosome region, to obtain at least two segments in the target chromosome region that use the gap as an interval, where a coverage depth value of a locus in the gap is less than a first threshold, the gap is a segment or a locus in the target chromosome region, and the at least two segments do not include the gap; determine some or all of the at least two segments in the target chromosome region as a target segment, where there are at least two target segments; use a weighted average value of coverage depth values of the target segments as a parameter that is of the target chromosome region and that is used for resource allocation, where the coverage depth of the target segment is an average coverage depth of loci in the target segment; and obtain the parameter value that is of the target chromosome region and that is used for resource allocation.

With reference to the second or the third possible implementation of the second aspect, in a fourth possible implementation of the second aspect, the obtaining unit is configured to use, as the target segment, at least one of a segment that is in the at least two segments in the target chromosome region and in which a quantity of sequenced reads meets a preset quantity requirement or a segment that is in the at least two segments in the target chromosome region and in which an average coverage depth of loci meets a preset coverage depth requirement.

With reference to the third possible implementation of the second aspect, in a fifth possible implementation of the second aspect, the obtaining unit is configured to calculate the weighted average value of the coverage depth values of the target segments by using a ratio of a length value of a target segment of the target segments to a length value of the target chromosome region as a weight value of a coverage depth value of the target segment.

With reference to any one of the second aspect or the foregoing possible implementations of the second aspect, in a sixth possible implementation of the second aspect, the obtaining unit is further configured to obtain an average value of respective parameter values that are of at least two chromosome regions and that are used for resource allocation; and the allocation unit is configured to: obtain, according to the parameter value that is obtained by the obtaining unit and that is of the target chromosome region and that is used for resource allocation and the average value, obtained by the obtaining unit, of the respective parameter values that are of the at least two chromosome regions and that are used for resource allocation, a deviation of the parameter value that is of the target chromosome region and that is used for resource allocation from the average value of the parameter values that are of the at least two chromosome regions and that are used for resource allocation; and allocate the computing resource to the operation according to the deviation.

With reference to the sixth possible implementation of the second aspect, in a seventh possible implementation of the second aspect, the at least two chromosome regions include the target chromosome region.

With reference to the sixth or the seventh possible implementation of the second aspect, in an eighth possible implementation of the second aspect, the deviation includes a ratio of the weighted average value of the coverage depth values of the target segments to a weighted average value of respective coverage depth values of the at least two chromosome regions; and the coverage depth of the chromosome region includes a weighted average value of respective coverage depth values of loci in at least two segments in the chromosome region, or includes an average coverage depth of loci in the chromosome region.

With reference to the sixth or the seventh possible implementation of the second aspect, in a ninth possible implementation of the second aspect, the deviation includes a ratio of the quantity value of the sequenced reads in the target chromosome region to an arithmetic average value of respective quantity values of sequenced reads in the at least two chromosome regions.

With reference to any one of the sixth to the ninth possible implementations of the second aspect, in a tenth possible implementation of the second aspect, the allocation unit is configured to adjust, according to the deviation, an initial computing resource used for implementing the operation, to obtain the computing resource.

According to a third aspect, a resource allocation apparatus for gene analysis is provided. The apparatus includes a memory and a processor. The memory is configured to store an instruction, and the processor is configured to execute the instruction stored in the memory. When the processor executes the instruction stored in the memory, the processor performs the method according to the first aspect or any possible implementation of the first aspect.

According to a fourth aspect, a computer storage medium is provided. The computer storage medium stores program code, and the program code is used to instruct to perform the method according to the first aspect or any possible implementation of the first aspect.

BRIEF DESCRIPTION OF DRAWINGS

FIG. 2 is a schematic flowchart of a resource allocation method according to an embodiment of this application;

FIG. 3 is a schematic diagram of a resource allocation method according to an embodiment of this application;

DESCRIPTION OF EMBODIMENTS

Figure 1:
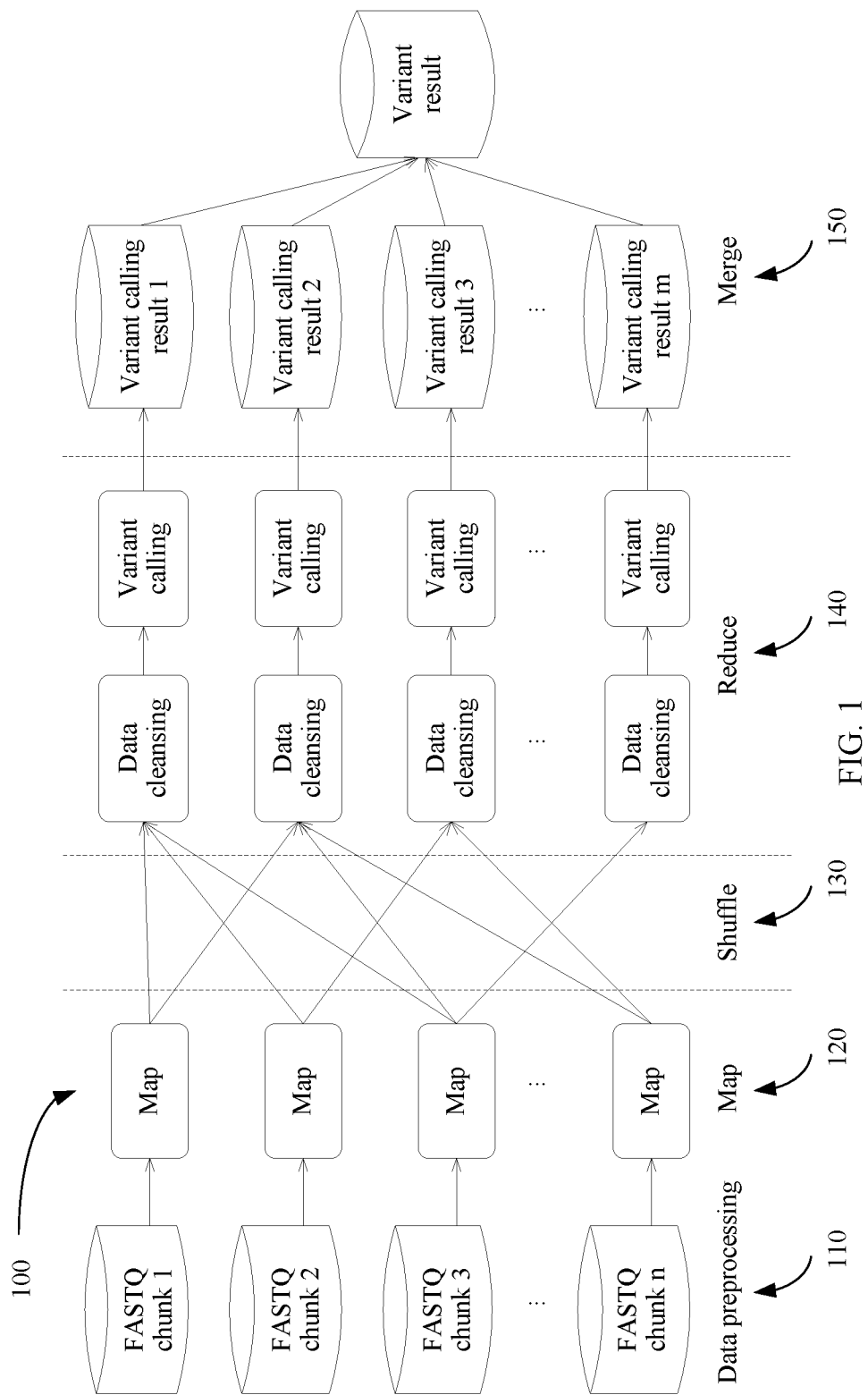
FIG. 1 is a schematic diagram of an application scenario according to an embodiment of this application.

The following describes the technical solutions in the embodiments of this application with reference to the accompanying drawings in the embodiments of this application.

Terms related in the embodiments of this application are described below for understanding instead of limitation.

A gene is a DNA sequence carrying hereditary information, is a basic hereditary unit of character controlling, and is also a base sequence with functionality. The gene expresses the carried hereditary information by directing protein synthesis, to control character (disparity) expression of a biont.

A DNA is a long-chain polymer, and composition units are referred to as four types of deoxyribonucleotides. The deoxyribonucleotide includes a deoxyribose (pentose), a phosphoric acid, and a base (Base). The deoxyribose and the phosphoric acid are connected by using an ester bond, to form an external long-chain skeleton. Each sugar molecule is internally connected to one of four types of bases. A sequence formed by arranging these bases along a long DNA chain may form hereditary code, and the hereditary code is a basis for composing a protein amino acid sequence. Bases that form the deoxyribonucleic acid are adenine (Adenine, A), thymine (Thymine, T), cytosine (Cytosine, C), and guanine (Guanine, G), and four corresponding types of deoxyribonucleotides are respectively deoxyadenosine monophosphate (dAMP), deoxythymidine monophosphate (dTMP), deoxycytidine monophosphate (dCMP), and deoxyguanosine monophosphate (dGMP).

The DNA is in a double-stranded structure, that is, a base on one strand appears in pair with a base on a corresponding location on the other strand. A base pair (Base Pair, BP) is formed according to a rule of combining A and T and combining C and G. Generally, the BP is used as a length unit of the DNA, and locations of A, T, C, and G in the DNA are referred to as loci. In a computer system, characters A, T, C, and G respectively represent the four types of bases, and each character occupies one byte. Therefore, a byte is also used as a length unit of the base sequence.

A chromosome (chromosome) is a main carrier of the DNA. Chromosomes of human beings appear in pairs, and are also referred to as diploids. A somatic cell of a normal person has 22 pairs of euchromosomes (Chr 1 to Chr 22) and one pair of sex chromosomes (Chr X and Chr Y) in total, and a chromosome number is a natural unit of gene region division.

Gene analysis includes three steps: DNA sequencing, DNA sequence assembly and variant calling, and gene annotation and analysis.

The DNA sequencing is a process of determining nucleotide arrangement order in a DNA molecule. In the DNA sequencing, a genetic sequencing technology based on massive parallel sequencing may be used.

In this sequencing technology, to increase a sequencing speed, a DNA is divided into segments with lengths of tens to hundreds of bases, and then a sequencer simultaneously sequences dozens to millions of segments. A base symbol sequence that is output after sequencing may be referred to as a read.

Generally, to improve sequencing accuracy and coverage (Coverage), repeated sequencing is performed on a target region to increase a sequencing depth.

The coverage is a percentage of base loci observed by means of sequencing in a to-be-sequenced target chromosome region. The sequencing depth is a ratio of a total base quantity obtained by means of sequencing to a length of a to-be-sequenced genome. The sequencing depth is approximately positively correlated with the coverage. It is generally considered that when the sequencing depth is at least 18×, relatively high accuracy can be achieved. A common whole-gene sequencing depth is 30× to 80×, and a sequencing depth for a region related to a specific disease may reach 100× to 10000×, where x represents a multiple/a depth, that is, a quantity of times for which a locus in the target chromosome region is covered by a read.

In a sequencing process, a DNA segment may be "lost". It may be considered that the coverage is mainly used for estimating a "loss" percentage. To avoid the loss, the DNA is replicated and sequenced multiple times, to increase the "sequencing depth", so that a "coverage depth" of an output result is increased.

The DNA sequence assembly and variant calling is a process in which scattered base sequence reads (Read) that are output by the sequencer are assembled into a complete DNA sequence by using a computer method, and a variant base locus is found by comparing the DNA sequence with a reference DNA.

The read is a character string with a length of dozens to hundreds of bytes. Original coordinates of the read in the DNA can be determined only after the read is mapped (Map) to a reference sequence. Because a human DNA has many repeated base sequences, some reads may be mapped to multiple locations, or multiple reads that are output by means of depth sequencing may be mapped to a same location, or multiple reads are mapped to a same location because of another reason. Therefore, a deduplication operation may be performed. The deduplication operation is used to remove a read that has same coordinates, a same length, and same content, so as to simplify data. Then, a local realignment operation may be performed, that is, an indel (Indel) variant is called, and local realignment (Local Realignment) is performed around the indel variant to recalibrate read coordinates. Then, a variant calling operation may be performed, that is, a sequencing quality score (Quality Score) and a mapping quality score of the read are analyzed, and a variant is called (Call Variants) by means of comparison with a reference sequence.

To optimize analysis quality, phases such as a filtering (Filter) operation and a base quality score recalibration (Base Quality Score Recalibration) operation may be added among the foregoing mapping operation, deduplication operation, and variant calling operation.

The gene annotation and analysis means that a sequencing result is analyzed and a gene and a function of the gene are identified by using a bioinformatics method and with reference to proteomics and transcriptomics, and a relationship between a variant and a related disease is found.

Among the three indispensable stages of gene analysis, the DNA sequence assembly and variant calling is a phase that requires large computing overheads. To reduce time overheads of gene analysis, a parallel computing framework may be used to construct an extensible gene analysis pipeline, for example, a parallel computing framework such as Hadoop or Spark may be used. The parallel computing framework such as Hadoop or Spark is designed mainly for homogeneous cluster nodes, and it is assumed that execution overheads of parallel tasks are balanced. However, after one or more processing steps are performed on DNA sequencing data, an obvious counting deviation occurs between a data amount of each task unit and a computing time of each task unit. Consequently, a "long tail" problem caused by a small quantity of complex computing tasks occurs, that is, an overall analysis task cannot end in time because some sub-tasks delay the computing time.

For clearer understanding of this problem, referring to FIG. 1, the following briefly describes the DNA sequence assembly and variant calling with reference to a Halvade framework 100. A Halvade system is a MapReduce-style distributed gene analysis pipeline application framework developed based on a Hadoop computing framework. In the abstract, a method thereof may also be implemented in a Spark computing framework.

In FIG. 1, in a data preprocessing (Data Preprocessing) stage (110), a FASTQ file used to store reads (reads) is segmented into n chunks of approximately 60 MB, and the n chunks are uploaded to a distributed file system. In a map (Map) stage (120), operating nodes read data from the distributed file system and concurrently execute independent read map tasks for each chunk. In a shuffle (Shuffle) stage (130), mapped reads are sorted and distributed to m reduce (Reduce) task units. Each reduce task (140) processes only a read in a specified chromosome region, and m may be equal or not equal to n. Finally, variant calling results that are output in the reduce tasks are merged (Merge) (150) into a uniform VCF file.

Each reduce task is corresponding to a specified segment of chromosome region. A task in a reduce stage is divided into a data cleansing step and a variant calling step. Data cleansing includes operations such as deduplication, local realignment, and base quality recalibration.

A quantity of map tasks may be determined by a quantity of chunks of FASTQ data. A quantity of reduce tasks may be determined by a quantity of chromosome regions. A quantity of map tasks or reduce tasks that are concurrently performed may be determined by cluster resources. It should be understood that FASTQ is a format of storing a read in the embodiments of this application, but is not limited in the embodiments of this application.

In the map stage, BWA MEM or BWA ALN+BWA SAMPE may be used in Halvade to map a read, and sequenced read data in a SAM format is output. Shuffled read data may be deduplicated by using an elPrep tool or a Picard tool in the reduce stage, and data in a BAM format is output. Then a GATK toolset may perform indel point realignment, base quality recalibration, and variant calling. HaplotypeCaller is a variant calling tool that has better accuracy but higher computing complexity than UnifiedGenotyper.

Reads output by a sequencer have asymmetrical coverage depths in different chromosome regions. For example, after a mapping operation is performed on a base sequence whose average sequencing depth is 60×, actual coverage depths of different chromosome regions are from zero to thousands (or event higher).

In a parallel computing framework (such as Hadoop or Spark), a data distribution rule of shuffled data in the reduce stage needs to be determined before a map task is started. In Halvade, a chromosome region with a fixed length is used as a basis for read distribution. Consequently, data amounts and computing amounts of different reduce task processing are severely unbalanced. Therefore, a disadvantage of Halvade is that balanced computing resources are allocated to all tasks and an analysis time "long tail" problem caused by a task deviation cannot be resolved. Time overheads of a small quantity of complex reduce tasks may be at least ten times of an average task time, and 1% of computing tasks may delay an entire analysis time by 20% to 50%.

Therefore, this application provides a resource allocation method, to properly allocate a computing resource.

FIG. 2 is a schematic flowchart of a resource allocation method 200 according to an embodiment of this application. As shown in FIG. 2, the method 200 includes step 210 and step 220.

In step 210, a parameter value that is of a target chromosome region and that is used for resource allocation is obtained according to a sequenced read in the target chromosome region.

In step 220, a computing resource is allocated, according to the parameter value that is of the target chromosome region and that is used for resource allocation, to an operation in a cleansing and variant calling task that is in the gene analysis and that is performed on the sequenced read in the target chromosome region.

Optionally, in this embodiment of this application, a chromosome region may be obtained by means of pre-division. One chromosome may be used as one chromosome region, or a partial region of one chromosome may be used as one chromosome region, or multiple chromosomes may be used as one chromosome region. Then a computing resource may be allocated to an operation in a cleansing and variant calling task for a sequenced read by using one chromosome region as a whole.

Optionally, this embodiment of this application may be applied to a MapReduce framework. In the MapReduce framework, the cleansing and variant calling task for the sequenced read may be referred to as a reduce task. Certainly, this embodiment of this application may be applied to another framework.

Optionally, the cleansing and variant calling task for the sequenced read may include at least one of a deduplication operation, a local realignment operation, a filtering operation, a base quality score recalibration operation, or a variant calling operation.

In this embodiment of this application, the sequenced read is a read that has definite chromosome coordinates after undergoing mapping processing.

Optionally, in this embodiment of this application, a parameter that is of the target chromosome region and that is used for resource allocation may include at least one of a quantity of sequenced reads in the target chromosome region or an average coverage depth of loci in the target chromosome region.

A quantity of sequenced reads in a chromosome region is a quantity of sequenced reads that cover the chromosome region. If only some bases of a sequenced read belong to the chromosome region, a quantity value of the sequenced read may be determined as 1, or a quantity value of the sequenced read may be determined as less than 1 such as 0.6 according to a percentage of the sequenced read in the chromosome region, that is, 60% of bases in the sequenced read belong to the chromosome region.

An average coverage depth value in loci in the chromosome region may be calculated in the following manner: A sum of length values of all sequenced reads that cover the chromosome region is calculated, the sum is divided by a length value of the chromosome region, and a quotient value is used as the average coverage depth value of the loci in the chromosome region. A length of the sequenced read and the length of the chromosome region may use a quantity of loci as a unit, for example, if the chromosome region includes 100 loci, the length value of the chromosome region is a length of 100 loci.

In this embodiment of this application, the chromosome region may be divided into multiple segments, and some or all of the segments are selected as a target segment.

Optionally, a parameter that is of the target chromosome region and that is used for resource allocation may include at least one of a quantity of target segments in the target chromosome region, a length of the target segment, a quantity of sequenced reads in the target segment, or an average coverage depth of loci in the target segment.

The quantity of sequenced reads in the target segment is a quantity of sequenced reads that cover the target segment.

The length of the target segment may be a quantity of loci in the target segment.

The average coverage depth value of the loci in the target segment may be calculated in the following manner: A sum of length values of the sequenced reads in the target segment is calculated, the sum is divided by a length value of the target segment, and a quotient value is used as the average coverage depth value of the loci in the target segment.

Optionally, a weighted average value of coverage depth values of target segments in the target chromosome region. The coverage depth of the target segment is an average coverage depth of loci in the target segment. In this case, the target chromosome region includes at least two target segments.

The weighted average value of the coverage depth values of the target segments may be obtained by performing weighting processing on an average coverage depth value of loci in all the target segments.

For example, the weighted average value of the coverage depth values of the target segments is determined by using, as a weight value, a ratio of a length value of each target segment to a sum of length values of the target segments in the target chromosome region.

The target chromosome region includes k target segments. It is assumed that coverage depth values of the k target segments are separately $d_1$ to $d_k$, length values are separately $l_1$ to $l_k$, and a value of a sum of the lengths is $L=l_1+l_2+\ldots+l_k$. A method for calculating a weighted coverage depth value d-region may be: d-region=$d_1 \times l_1/L + d_2 \times l_2/L + \ldots + d_k \times l_k/L$.

Optionally, in this embodiment of this application, the target segment may be determined in the following manner: A coverage depth value of a locus in the target chromosome region is obtained according to a quantity value of sequenced reads that cover the locus in the target chromosome region; a gap in the target chromosome region is determined according to the coverage depth value of the locus in the target chromosome region, to obtain at least two segments in the target chromosome region that use the gap as an interval, where a coverage depth value of a locus in the gap is less than a first threshold, the gap is a segment or a locus in the target chromosome region, and the at least two segments do not include the gap; and some or all of the at least two segments in the target chromosome region are determined as the target segment.

Any locus whose coverage depth value is less than the first threshold may be used as a locus in the gap, or N (N is greater than or equal to 2) loci may be used as a unit, and any N loci of which an average coverage depth value is less than the first threshold are used as a whole and used as the gap.

The N loci may be selected in a loci overlapping manner or in a loci non-overlapping manner.

For example, it is assumed that there are 100 loci, N is 5, and selection is performed in the loci non-overlapping manner. An average coverage depth value of loci 1 to 5 may be determined, and then an average coverage depth value of loci 6 to 10 is determined, and so on. Any five loci of which an average coverage depth value is less than the first threshold are used as a gap for segment division.

For another example, it is assumed that there are 100 loci, N is 5, and selection is performed in the loci overlapping manner. An average coverage depth value of loci 1 to 5 may be determined, an average coverage depth value of loci 2 to 6 is determined, and an average coverage depth value of loci 3 to 7 is determined. Any five loci of which an average coverage depth value is less than the first threshold are used as a gap for segment division. For example, it is assumed that the average coverage depth value of the loci 1 to 5 and the average coverage depth value of the loci 2 to 6 are each less than the first threshold, and the loci 1 to 6 may be used as the gap.

A coverage depth value of a locus may be obtained by determining a quantity of reads that cover the locus. Optionally, the first threshold may be set according to an actual case, for example, according to a counting computing amount that a computing system can bear. For example, a smaller counting computing amount that the computing system can bear indicates that a higher threshold may be set.

Optionally, when the target segment is selected from the at least two segments obtained by dividing the chromosome region, the target segment may be selected according to at least one of a quantity of sequenced reads in the at least two segments or an average coverage depth of loci in the at least two segments.

At least one of a segment that is in the at least two segments in the target chromosome region and in which a quantity of sequenced reads meets a preset quantity requirement or a segment that is in the at least two segments in the target chromosome region and in which an average coverage depth of loci meets a preset coverage depth requirement is used as the target segment.

For example, each of k segments that are in the at least two segments and that have a maximum average coverage depth of loci is determined as the target segment, or each segment that is in the at least two segments and in which an average coverage depth value of loci is greater than a second threshold is determined as the target segment, or each of k segments that are in the at least two segments and have a maximum quantity of sequenced reads is determined as the target segment, or each segment that is in the multiple segments and in which a quantity value of sequenced reads is greater than a third threshold is determined as the target segment.

Therefore, in this embodiment of this application, a gap in which an average coverage depth value of loci is less than a threshold is used as an interval, to divide the chromosome region into multiple segments, and the target segment is selected from the multiple segments. A parameter of the target segment is used as the parameter used for resource allocation, and a segment that has a relatively large quantity of reads or a relatively large coverage depth may be locally counted, to better determine a deviation status of the parameter that is in the target chromosome region and that is used for resource allocation.

In addition, the segment that is in the multiple segments and has a relatively large coverage depth or a relatively large quantity of reads is further selected as the target segment, so that parameters referenced during resource allocation are more meaningful.

In this embodiment of this application, the target segment in the chromosome region may be determined in another manner. For example, specific loci are selected as a start point and an end point of the target segment. For example, the second locus in the chromosome region is selected as a start point of the first target segment, and the $50^{th}$ locus is selected as an end point of the target segment; the $102^{nd}$ locus in the chromosome region is selected as a start point of the second target segment, and the $150^{th}$ locus is selected as an end point of the second target segment; the $202^{nd}$ locus in the chromosome region is selected as a start point of the third target segment, and the $250^{th}$ locus is selected as an end point of the third target segment; and so on. In this case, at least one of the quantity of sequenced reads in the target segment, the average coverage depth of the loci in the target segment, or the weighted average value of the coverage depth values of the target segments in the target chromosome region may be used as the parameter used for resource allocation.

Optionally, the computing resource mentioned in this embodiment of this application may include at least one of a central processing unit (CPU) resource, a memory resource, a graphics processing unit (Graphics Processing Unit, GPU) resource, or a field programmable gate array (Field Programmable Gate Array, FPGA) resource.

Optionally, in this embodiment of this application, an average value of respective parameter values that are of at least two chromosome regions and that are used for resource allocation may be obtained; a deviation of the parameter value that is of the target chromosome region and that is used for resource allocation from the average value of the respective parameter values that are of the at least two chromosome regions and that are used for resource allocation is obtained according to the parameter value that is of the target chromosome region and that is used for resource allocation and the average value of the respective parameter values that are of the at least two chromosome regions and that are used for resource allocation; and the computing resource is allocated to the operation according to the deviation.

In this embodiment of this application, the foregoing deviation may be determined by using a ratio of the parameter value that is of the target chromosome region and that is used for resource allocation to the average value of the respective parameter values that are of the at least two chromosome regions and that are used for resource allocation, and the computing resource is allocated according to the deviation.

The ratio of the parameter value that is of the target chromosome region and that is used for resource allocation to the average value of the respective parameter values that are of the at least two chromosome regions and that are used for resource allocation may be a value obtained after the parameter value that is of the target chromosome region and that is used for resource allocation is divided by the average value of the respective parameter values that are of the at least two chromosome regions and that are used for resource allocation. In this case, a quantity value of resources allocated to the target chromosome region may be positively correlated with the ratio.

Alternatively, the ratio of the parameter value that is of the target chromosome region and that is used for resource allocation to the average value of the respective parameter values that are of the at least two chromosome regions and that are used for resource allocation may be a value obtained after the average value of the respective parameter values that are of the at least two chromosome regions and that are used for resource allocation is divided by the parameter value that is of the target chromosome region and that is used for resource allocation. In this case, a quantity value of resources allocated to the target chromosome region may be negatively correlated with the ratio.

Optionally, the foregoing average value may be an arithmetic average value or a weighted average value.

In an implementation, the parameter that is of the target chromosome region and that is used for resource allocation includes the quantity of sequenced reads in the target chromosome region. In this case, the computing resource may be allocated according to a ratio of the quantity value of the sequenced reads in the target chromosome region to an arithmetic average value of respective quantity values of sequenced reads in the at least two chromosome regions.

In this embodiment of this application, a deviation of the quantity value of the sequenced reads in the target chromosome region from the arithmetic average value of the respective quantity values of the sequenced reads in the at least two chromosome regions may be determined by using a deviation of a size of an input file in the target chromosome region from an average size of input files in the at least two chromosome regions.

In another implementation, the parameter that is of the target chromosome region and that is used for resource allocation includes the average coverage depth value of the loci in the target chromosome region. In this case, the computing resource may be allocated according to a ratio of the average coverage depth value of the loci in the target chromosome region to an arithmetic average value of respective average coverage depth values of loci in the at least two chromosome regions.

In another implementation, the parameter that is of the target chromosome region and that is used for resource allocation includes the quantity of target segments, target segment division may be performed on a non-target chromosome region in the at least two chromosome regions according to a target segment division rule that is the same as that used in the target chromosome region, and an arithmetic average value of respective quantity values of target segments in the at least two chromosome regions is determined. In this case, the computing resource may be allocated according to a ratio of the quantity value of the target segments in the target chromosome region to the arithmetic average value of the respective quantity values of the target segments in the at least two chromosome regions.

In another implementation, the parameter that is of the target chromosome region and that is used for resource allocation includes the length of the target segment, target segment division may be performed on a non-target chromosome region in the at least two chromosome regions according to a target segment division rule that is the same as that used in the target chromosome region, and a total length value of target segments in each chromosome region is determined. In this case, the computing resource may be allocated according to a ratio of a total length value of the target segments in the target chromosome region to an arithmetic average value of respective total length values of the target segments in the at least two chromosome regions.

In another implementation, the parameter that is of the target chromosome region and that is used for resource allocation includes the quantity of sequenced reads in the target segment, target segment division may be performed on a non-target chromosome region in the at least two chromosome regions according to a target segment division rule that is the same as that used in the target chromosome region, and a total quantity of reads in a target segment in each chromosome region is determined. In this case, the computing resource may be allocated according to a ratio of a total quantity of sequenced reads in the target segment in the target chromosome region to an arithmetic average value of respective total quantities of sequenced reads in target segments in the at least two chromosome regions.

In another implementation, the parameter that is of the target chromosome region and that is used for resource allocation includes the average coverage depth of the loci in the target segment, an average coverage depth value of loci in all target segments in the target chromosome region may be calculated, target segment division is performed on a non-target chromosome region in the at least two chromosome regions according to a target segment division rule that is the same as that used in the target chromosome region, and an average coverage depth value of loci in all target segments in each non-target chromosome region in the at least two chromosome regions is determined. In this case, the computing resource may be allocated according to a ratio of the average coverage depth value of the loci in all the target segments in the target chromosome region to an arithmetic average value of respective average coverage depths of loci in target segments in the at least two chromosome regions.

In another implementation, the parameter that is of the target chromosome region and that is used for resource allocation includes the weighted average value of the coverage depth values of the target segments in the target chromosome region. In this case, the computing resource may be allocated according to a ratio of the weighted average value of the coverage depth values of the target segments in the target chromosome region to a weighted average value of respective coverage depth values of the at least two chromosome regions. The coverage depth of the chromosome region includes a weighted average value of respective coverage depth values of loci in at least two segments in the chromosome region, or includes an average coverage depth of loci in the chromosome region.

Optionally, segments in the non-target chromosome region in the at least two chromosome regions may be divided in a manner that is the same as a manner of dividing target segments in the target chromosome region.

Optionally, weighted coverage depth values of at least two segments in the non-target chromosome region may be calculated by using, as a weight value, a ratio of a length value of each of the at least two segments to a total length value of the at least two segments.

Optionally, a weighted average value of respective coverage depth values of the at least two chromosome regions may be calculated by using, as a weight value, a ratio of a length value of each of the at least two chromosome regions to a total length value of the at least two chromosome regions.

It should be understood that in this embodiment of this application, alternatively, the deviation may be determined according to a difference between the parameter value that is of the target chromosome region and that is used for resource allocation and the average value of the respective parameter values that are of the at least two chromosome regions and that are used for resource allocation, or may be determined in another manner provided that a degree of the deviation of the parameter value that is of the target chromosome region and that is used for resource allocation from the average value of the respective parameter values that are of the at least two chromosome regions and that are used for resource allocation can be reflected.

It should be further understood that in addition to allocating the resource according to the deviation of the parameter value that is of the target chromosome region and that is used for resource allocation from the average value of the respective parameter values that are of the at least two chromosome regions and that are used for resource allocation, the computing resource may be allocated in another manner. For example, the resource is allocated according to the parameter value that is of the target chromosome region and that is used for resource allocation, and the average value of the respective parameter values that are of the at least two chromosome regions and that are used for resource allocation is not considered. For example, it is assumed that the target chromosome region has 100 sequenced reads, and a computing resource required by each sequenced read may be determined, to determine resources required by the 100 sequenced reads. For example, a coverage depth value of a locus in the target chromosome region is in a specific function relationship with a quantity value of required computing resources. A resource is allocated according to the function relationship. In the function relationship, the coverage depth value is positively correlated with the quantity value of the computing resources.

It should be further understood that, although the resource is allocated according to one type of parameter in the foregoing examples, the resource may be allocated by considering multiple parameters in this embodiment of this application, for example, both the average coverage depth of the loci in the target chromosome region and the average coverage depth of the loci in the target segment in the target chromosome region are considered.

In this embodiment of this application, an initial computing resource used for implementing at least one operation in the cleansing and variant calling task for the sequenced read is adjusted to obtain a computing resource used for the operation.

A resource may be pre-allocated to the at least one operation in the cleansing and variant calling task for the sequenced read, and then the pre-allocated resource is adjusted according to the parameter value that is of the target chromosome region and that is used for resource allocation.

Alternatively, in this embodiment of this application, no resource may be pre-allocated to the operation in the cleansing and variant calling task for the sequenced read, and a resource may be directly allocated according to the parameter value that is of the target chromosome region and that is used for resource allocation.

In this embodiment of this application, during resource allocation, if it is determined that a task requires relatively more computing resources, some of resources that are pre-allocated to a task that requires a relatively small computing amount may be reallocated to the task that requires relatively more computing resources. Alternatively, computing resources pre-allocated to a task that requires relatively fewer computing resources may not change, but instead, another computing resource (a spare computing resource that has not been pre-allocated) is allocated to a task that requires relatively more computing resources.

In this embodiment of this application, before the cleansing and variant calling task for the sequenced read is performed, a resource may be allocated according to one or more types of the foregoing parameter values used for resource allocation, and then all operations in the cleansing and variant calling task for the sequenced read are performed. In this case, resource allocation implementation can be simplified.

For example, as shown in FIG. 3, parameters may be counted after mapping processing and before data cleansing, that is, a parameter value used for resource allocation is determined. The parameter value is sent to a deviation scheduler. The deviation scheduler determines a resource allocation plan according to the parameter value, and then notifies a task scheduler of the resource allocation plan. The task scheduler instructs a corresponding task execution module to cleanse data according to an updated task resource, and instructs the corresponding task execution module to perform variant calling by using the updated task resource.

A resource manager may be responsible for tracking a use status of a system computing resource. The system computing resource includes a CPU core, a memory, a GPU, an FPGA, and the like. A resource quota needs to be obtained first before each operation is started and performed. The resource manager may preferentially allocate a resource according to a resource allocation plan of a resource allocation apparatus and may allocate a resource with overload if necessary, and start a deviation step in time when available resources are insufficient.

Alternatively, a resource may be allocated before each operation in the cleansing and variant calling task for the sequenced read, and a used parameter may be determined according to a corresponding operation. For example, if the deduplication operation, the filtering operation, the local realignment operation, and the base quality score recalibration operation are in a stronger correlation with the quantity of sequenced reads in the chromosome region, and the variant calling operation is in a stronger correlation with the weighted average value of the coverage depth values of the target segments, and before a corresponding operation is performed, a resource may be allocated to the operation according to a parameter value with a relatively strong correlation. In this case, a resource can be accurately allocated.

Figure 4:
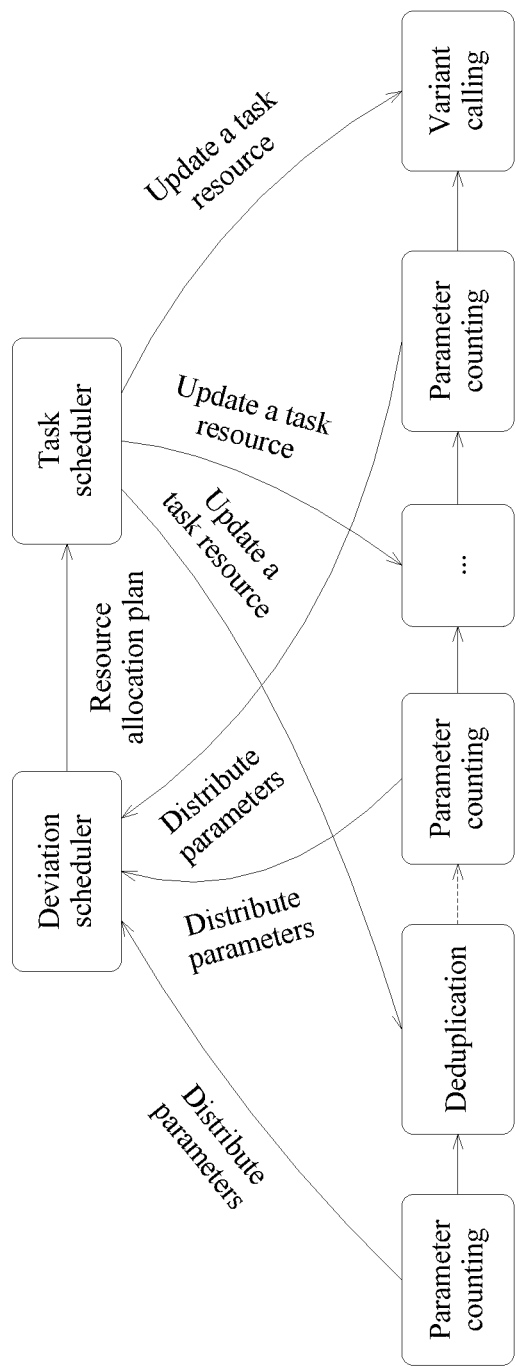
FIG. 4 is a schematic diagram of a resource allocation method according to an embodiment of this application.

For example, as shown in FIG. 4, a parameter is counted (that is, the parameter value that is of the target chromosome region and that is used for resource allocation is determined) after mapping processing and before each operation such as the deduplication operation, the local realignment operation (not shown), or the variant calling operation. Then a deviation scheduler determines a resource allocation plan according to the parameter value that is of the target chromosome region and that is used for resource allocation, and then notifies a task scheduler of the resource allocation plan, and the task scheduler allocates a resource to a reduce task.

It should be understood that FIG. 3 and FIG. 4 show task resource updating, that is, there is pre-configured resource allocation. However, this is not limited in this embodiment of this application. In this embodiment of this application, there may not be pre-configured resource allocation, and a resource is directly allocated according to the parameter value that is of the target chromosome region and that is used for resource allocation.

Optionally, in this embodiment of this application, when there is a pre-configured computing resource, a resource allocation plan may be updated in the following calculation manner:

$$R\text{-update}=R+[t\times(x\text{-region}/x\text{-average}-1)\times P]=<r\text{-cpu\_cores}+[t\times(x\text{-region}/x\text{-average}-1)\times p\text{-cpu\_cores}],$$

$$r\text{-mem}+[t\times(x\text{-region}/x\text{-average}-1)\times p\text{-mem}], r\text{-mem}+[t\times(x\text{-region}/x\text{-average}-1)\times p\text{-mem}],$$

$$r\text{-gpu}+[t\times(x\text{-region}/x\text{-average}-1)\times p\text{-gpu}],$$

$$r\text{-fpga}+[t\times(x\text{-region}/x\text{-average}-1)\times p\text{-fpga}]>, \text{where}$$

x-region is the parameter value that is of the target chromosome region and that is used for resource allocation; x-average is the average value of the parameter values that are of the at least two chromosome regions and that are used for resource allocation; R<r-cpu_cores, r-mem, r-gpu, r-fpga> is a basic resource allocation plan of one or more operations in the cleansing and variant calling task for the sequenced read, and r-cpu_cores, r-mem, r-gpu, and r-fpga are respectively used to describe a CPU core resource, a memory resource, a GPU resource, and an FPGA resource that are pre-allocated and required for performing the one or more operations; P<p-cpu_cores, p-mem, p-gpu, p-fpga> describes a resource allocation adjustment unit of the one or more operations; t is an adjustment parameter; and [ ] is a rounding operator.

For clearer understanding of this application, the following describes, with reference to several specific parameters, how to allocate a resource with reference to the parameter value that is of the target chromosome region and that is used for resource allocation.

For example, if the parameter that is of the target chromosome region and that is used for resource allocation is the quantity of sequenced reads in the target chromosome region, an average value of respective quantity values of sequenced reads in the at least two chromosome regions may be obtained. Optionally, the at least two chromosome regions include the target chromosome region. A computing resource is allocated to the at least one operation in the cleansing and variant calling task for the sequenced read in the target chromosome region according to a ratio of the quantity value of the sequenced reads in the target chromosome region to the average value.

A calculation method for updating a resource allocation plan is:

$$R\text{-update}=R+[t\times(x\text{-region}/x\text{-average}-1)\times P]=<r\text{-cpu\_cores}+[t\times(x\text{-region}/x\text{-average}-1)\times p\text{-cpu\_cores}],$$

$$r\text{-mem}+[t\times(x\text{-region}/x\text{-average}-1)\times p\text{-mem}], r\text{-mem}+[t\times(x\text{-region}/x\text{-average}-1)\times p\text{-mem}],$$

$$r\text{-gpu}+[t\times(x\text{-region}/x\text{-average}-1)\times p\text{-gpu}],$$

$$r\text{-fpga}+[t\times(x\text{-region}/x\text{-average}-1)\times p\text{-fpga}]>, \text{where}$$

c-region is the quantity value of the sequenced reads in the target chromosome region; c-average is the average value of the respective quantity values of the sequenced reads in the at least two chromosome regions; R<r-cpu_cores, r-mem, r-gpu, r-fpga> is a basic resource allocation plan of one or more operations in the reduce task, and r-cpu_cores, r-mem, r-gpu, and r-fpga are respectively used to describe a CPU core resource, a memory resource, a GPU resource, and an FPGA resource that are pre-allocated and required for performing the one or more operations; P<p-cpu_cores, p-mem, p-gpu, p-fpga> describes a resource allocation adjustment unit of the one or more operations; t is an adjustment parameter; and [ ] is a rounding operator.

The deduplication operation, the filtering operation, the local realignment operation, and the base quality score recalibration operation are in a relatively strong correlation with a quantity of reads in a chromosome region. Therefore, before each of the deduplication operation, the filtering operation, the local realignment operation, and the base quality score recalibration operation, a resource is allocated according to a quantity value of sequenced reads that are in the chromosome region and that undergo previous processing, or a resource is allocated according to a quantity value of sequenced reads in a chromosome region only before the deduplication operation.

For another example, if the parameter that is of the target chromosome region and that is used for resource allocation includes the weighted average value of the coverage depth values of the target segments in the target chromosome region, the weighted average value of the respective coverage depth values of the at least two chromosome regions needs to be further obtained. A computing resource is allocated to the at least one operation in the cleansing and variant calling task for the sequenced read in the target chromosome region according to a ratio of the weighted average value of the coverage depth values of the target segments in the target chromosome region to the weighted average value of the respective coverage depth values of the at least two chromosome regions. A coverage depth of a chromosome region may include a weighted average value of respective coverage depth values of loci in at least two segments in the chromosome region, or include an average coverage depth of loci in the chromosome region.

A calculation method for updating a resource allocation plan is:

$$R\text{-update}=R+[t\times(x\text{-region}/x\text{-average}-1)\times P]=<r\text{-cpu\_cores}+[t\times(x\text{-region}/x\text{-average}-1)\times p\text{-cpu\_cores}],$$

$$r\text{-mem}+[t\times(x\text{-region}/x\text{-average}-1)\times p\text{-mem}], r\text{-mem}+[t\times(x\text{-region}/x\text{-average}-1)\times p\text{-mem}],$$

$$r\text{-gpu}+[t\times(x\text{-region}/x\text{-average}-1)\times p\text{-gpu}],$$

$$r\text{-fpga}+[t\times(x\text{-region}/x\text{-average}-1)\times p\text{-fpga}]>, \text{ where}$$

d-region is the weighted average value of the coverage depth values of the target segments in the target chromosome region; d-average is the weighted average value of the respective coverage depth values of the at least two chromosome regions; R<r-cpu_cores, r-mem, r-gpu, r-fpga> is a basic resource allocation plan of one or more operations in the cleansing and variant calling task for the sequenced read, and r-cpu_cores, r-mem, r-gpu, and r-fpga are respectively used to describe a CPU core resource, a memory resource, a GPU resource, and an FPGA resource that are pre-allocated and required for performing the one or more operations; P<p-cpu_cores, p-mem, p-gpu, p-fpga> describes a resource allocation adjustment unit of the one or more operations; t is an adjustment parameter; and [ ] is a rounding operator.

The variant calling operation is in a relatively strong correlation with the weighted average value of the coverage depth values of the target segments. Therefore, the target segments and the weighted average value of the coverage depth values of the target segments may be determined before the variant calling operation according to the quantity value of the sequenced reads that are in the chromosome region and that undergo the previous processing, and a resource is allocated.

It should be understood that the foregoing c-average and d-average may be calculated in real time by using a chromosome region counting result submitted by each reduce task, or may be calculated in advance according to a total quantity of sequenced reads output by means of mapping and information about a segmented chromosome region before the reduce task is started.

Therefore, in this embodiment of this application, a difference between computing amounts of chromosome region analysis tasks is determined according to sequenced reads in chromosome regions, and guidance is provided for a scheduling system so that the scheduling system preferentially allocates an advantaged computing resource to a complex analysis task, so as to improve overall performance of a gene analysis operation, improve use efficiency of computing resources in an analysis system, and generally reduce time overheads of the gene analysis operation.

Figure 5:
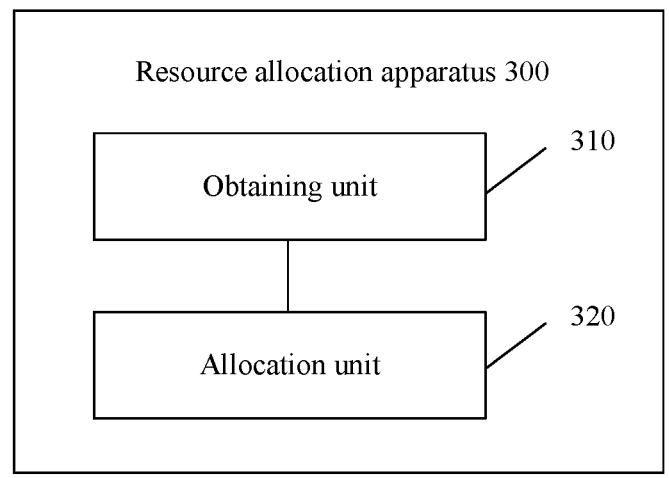
FIG. 5 is a schematic block diagram of a resource allocation apparatus according to an embodiment of this application.

FIG. 5 is a schematic block diagram of a resource allocation apparatus 300 for gene analysis according to an embodiment of this application. As shown in FIG. 5, the apparatus includes an obtaining unit 310 and an allocation unit 320. The obtaining unit 310 is configured to obtain, according to a sequenced read in a target chromosome region, a parameter value that is of the target chromosome region and that is used for resource allocation. The allocation unit 320 is configured to allocate, according to the parameter value that is of the target chromosome region and that is used for resource allocation, a computing resource to an operation in a cleansing and variant calling task that is in the gene analysis and that is performed on the sequenced read in the target chromosome region.

Optionally, a parameter that is of the target chromosome region and that is used for resource allocation includes at least one of a quantity of sequenced reads in the target chromosome region or an average coverage depth of loci in the target chromosome region.

Optionally, the obtaining unit is configured to: obtain a coverage depth value of a locus in the target chromosome region according to a quantity value of sequenced reads that cover the locus in the target chromosome region; determine a gap in the target chromosome region according to the coverage depth value of the locus in the target chromosome region, to obtain at least two segments in the target chromosome region that use the gap as an interval, where a coverage depth value of a locus in the gap is less than a first threshold, the gap is a segment or a locus in the target chromosome region, and the at least two segments do not include the gap; determine some or all of the at least two segments in the target chromosome region as a target segment; use at least one of a quantity of target segments, a length of the target segment, a quantity of sequenced reads in the target segment, or a coverage depth of the target segment as a parameter that is of the target chromosome region and that is used for resource allocation; and obtain the parameter value that is of the target chromosome region and that is used for resource allocation.

Optionally, the obtaining unit 310 is configured to: obtain a coverage depth value of a locus in the target chromosome region according to a quantity value of sequenced reads that cover the locus in the target chromosome region; determine a gap in the target chromosome region according to the coverage depth value of the locus in the target chromosome region, to obtain at least two segments in the target chromosome region that use the gap as an interval, where a coverage depth value of a locus in the gap is less than a first threshold, the gap is a segment or a locus in the target chromosome region, and the at least two segments do not include the gap; determine some or all of the at least two segments in the target chromosome region as a target segment, where there are at least two target segments; use a weighted average value of coverage depth values of the target segments as a parameter that is of the target chromosome region and that is used for resource allocation, where the coverage depth of the target segment is an average coverage depth of loci in the target segment; and obtain the parameter value that is of the target chromosome region and that is used for resource allocation.

Optionally, the obtaining unit 310 is configured to use, as the target segment, at least one of a segment that is in the at least two segments in the target chromosome region and in which a quantity of sequenced reads meets a preset quantity requirement or a segment that is in the at least two segments in the target chromosome region and in which an average coverage depth of loci meets a preset coverage depth requirement.

Optionally, the obtaining unit 310 is configured to calculate the weighted average value of the coverage depth values of the target segments by using a ratio of a length value of the target segment to a length value of the target chromosome region as a weight value of a coverage depth value of the target segment.

Optionally, the obtaining unit 310 is further configured to obtain an average value of respective parameter values that are of at least two chromosome regions and that are used for resource allocation. The allocation unit 320 is configured to: obtain, according to the parameter value that is obtained by the obtaining unit 310 and that is of the target chromosome region and that is used for resource allocation and the average value, obtained by the obtaining unit 310, of the respective parameter values that are of the at least two chromosome regions and that are used for resource allocation, a deviation of the parameter value that is of the target chromosome region and that is used for resource allocation from the average value of the respective parameter values that are of the at least two chromosome regions and that are used for resource allocation; and allocate the computing resource to the operation according to the deviation.

Optionally, the at least two chromosome regions include the target chromosome region.

Optionally, the deviation includes a ratio of the weighted average value of the coverage depth values of the target segments to a weighted average value of respective coverage depth values of the at least two chromosome regions. The coverage depth of the chromosome region includes a weighted average value of respective coverage depth values of loci in at least two segments in the chromosome region, or includes an average coverage depth of loci in the chromosome region.

Optionally, the deviation includes a ratio of the quantity value of the sequenced reads in the target chromosome region to an arithmetic average value of respective quantity values of sequenced reads in the at least two chromosome regions.

Optionally, the allocation unit 320 is configured to adjust, according to the deviation, an initial computing resource used for implementing the operation, to obtain the computing resource.

It should be understood that the apparatus 300 according to this embodiment of this application may implement a corresponding process in the method embodiment shown in FIG. 2 or in another optional embodiment (for example, that shown in FIG. 3 or FIG. 4). For brevity, details are not described herein again.

Figure 6:
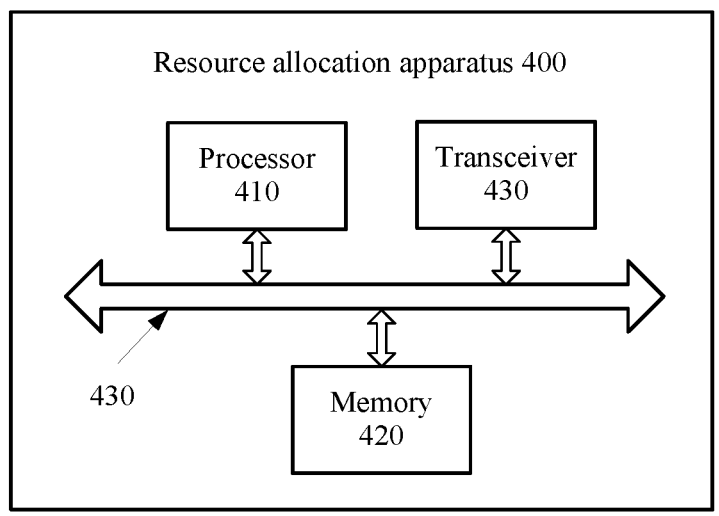
FIG. 6 is a schematic block diagram of a resource allocation apparatus according to an embodiment of this application.

FIG. 6 is a schematic block diagram of a resource allocation apparatus 400 for gene analysis according to an embodiment of this application.

As shown in FIG. 6, the apparatus 400 includes a processor 410 and a memory 420. The memory 420 is configured to store a program instruction. The processor 410 may invoke the program instruction stored in the memory 420, and may perform one or more steps in the embodiment shown in FIG. 2 or another optional implementation in the method embodiment.

The processor 410 may invoke the program instruction stored in the memory 420 to perform the following processing: obtaining, according to a sequenced read in a target chromosome region, a parameter value that is of the target chromosome region and that is used for resource allocation; and allocating, according to the parameter value that is of the target chromosome region and that is used for resource allocation, a computing resource to an operation in a cleansing and variant calling task that is in the gene analysis and that is performed on the sequenced read in the target chromosome region.

Optionally, a parameter that is of the target chromosome region and that is used for resource allocation includes at least one of a quantity of sequenced reads in the target chromosome region or an average coverage depth of loci in the target chromosome region.

Optionally, the processor 410 may invoke the program instruction stored in the memory 420 to perform the following processing: obtaining a coverage depth value of a locus in the target chromosome region according to a quantity value of sequenced reads that cover the locus in the target chromosome region; determining a gap in the target chromosome region according to the coverage depth value of the locus in the target chromosome region, to obtain at least two segments in the target chromosome region that use the gap as an interval, where a coverage depth value of a locus in the gap is less than a first threshold, the gap is a segment or a locus in the target chromosome region, and the at least two segments do not include the gap; determining some or all of the at least two segments in the target chromosome region as a target segment; using at least one of a quantity of target segments, a length of the target segment, a quantity of sequenced reads in the target segment, or a coverage depth of the target segment as a parameter that is of the target chromosome region and that is used for resource allocation; and obtaining the parameter value that is of the target chromosome region and that is used for resource allocation.

Optionally The processor 410 may invoke the program instruction stored in the memory 420 to perform the following processing: obtaining a coverage depth value of a locus in the target chromosome region according to a quantity value of sequenced reads that cover the locus in the target chromosome region; determining a gap in the target chromosome region according to the coverage depth value of the locus in the target chromosome region, to obtain at least two segments in the target chromosome region that use the gap as an interval, where a coverage depth value of a locus in the gap is less than a first threshold, the gap is a segment or a locus in the target chromosome region, and at least two segments do not include the gap; determining some or all of the at least two segments in the target chromosome region as a target segment, where there are at least two target segments; using a weighted average value of coverage depth values of the target segments as a parameter that is of the target chromosome region and that is used for resource allocation, where the coverage depth of the target segment is an average coverage depth of loci in the target segment; and obtaining the parameter value that is of the target chromosome region and that is used for resource allocation.

Optionally, the processor 410 may invoke the program instruction stored in the memory 420 to perform the following processing: using, as the target segment, at least one of a segment that is in the at least two segments in the target chromosome region and in which a quantity of sequenced reads meets a preset quantity requirement or a segment that is in the at least two segments in the target chromosome region and in which an average coverage depth of loci meets a preset coverage depth requirement.

Optionally, the processor 410 may invoke the program instruction stored in the memory 420 to perform the following processing: calculating the weighted average value of the coverage depth values of the target segments by using a ratio of a length value of the target segment to a length value of the target chromosome region as a weight value of a coverage depth value of the target segment.

Optionally, the processor 410 may invoke the program instruction stored in the memory 420 to perform the following processing: obtaining an average value of respective parameter values that are of at least two chromosome regions and that are used for resource allocation; obtaining, according to the parameter value that is of the target chromosome region and that is used for resource allocation and the average value of the respective parameter values that are of the at least two chromosome regions and that are used for resource allocation, a deviation of the parameter value that is of the target chromosome region and that is used for resource allocation from the average value of the respective parameter values that are of the at least two chromosome regions and that are used for resource allocation; and allocating the computing resource to the operation according to the deviation.

Optionally, the at least two chromosome regions include the target chromosome region.

Optionally, the deviation includes a ratio of the weighted average value of the coverage depth values of the target segments to a weighted average value of respective coverage depth values of the at least two chromosome regions. The coverage depth of the chromosome region includes a weighted average value of respective coverage depth values of loci in at least two segments in the chromosome region, or includes an average coverage depth of loci in the chromosome region.

Optionally, the deviation includes a ratio of the quantity value of the sequenced reads in the target chromosome region to an arithmetic average value of respective quantity values of sequenced reads in the at least two chromosome regions.

Optionally, the processor 410 may invoke the program instruction stored in the memory 420 to perform the following processing: adjusting, according to the deviation, an initial computing resource used for implementing the operation, to obtain the computing resource.

Optionally, as shown in FIG. 6, the apparatus 400 may further include a bus system 430, and the processor 410 and the memory 420 are connected by using the bus system 430. The processor 410 and the memory 420 may be connected in another manner, for example, be directly connected.

Optionally, as shown in FIG. 6, the apparatus 400 further includes a receiver 440, configured to transmit data to or receive data from another apparatus, for example, receive a sequenced read sent by the another apparatus, so that the processor may obtain, based on the sequenced read, the parameter value that is of the target chromosome region and that is used for resource allocation.

In this embodiment of this application, the processor 410 may be a central processing unit (central processing unit, CPU), a network processor (network processor, NP), or a combination of a CPU and an NP. The processor 410 may further include a hardware chip. The hardware chip may be an application-specific integrated circuit (application-specific integrated circuit, ASIC), a programmable logic device (programmable logic device, PLD), or a combination thereof. The PLD may be a complex programmable logical device (complex programmable logical device, CPLD), a field programmable gate array (field programmable gate array, FPGA), generic array logic (generic array logic, GAL), or any combination thereof.

In addition to a data bus, the bus system 430 may further include a power bus, a control bus, a status signal bus, and the like. For ease of denotation, the bus system 430 is indicated by using only one thick line in the figure. However, it does not indicate that there is only one bus or only one type of bus.

It should be understood that the apparatus 400 according to this embodiment of this application may implement a corresponding process in the method embodiment shown in FIG. 2 or in another optional embodiment. For brevity, details are not described herein again.

A person of ordinary skill in the art may be aware that, in combination with the examples described in the embodiments disclosed in this specification, units and algorithm steps may be implemented by electronic hardware or a combination of computer software and electronic hardware. Whether the functions are performed by hardware or software depends on particular applications and design constraint conditions of the technical solutions. A person skilled in the art may use different methods to implement the described functions for each particular application, but it should not be considered that the implementation goes beyond the scope of this application.

It may be clearly understood by a person skilled in the art that, for the purpose of convenient and brief description, for a detailed working process of the foregoing system, apparatus, and unit, refer to a corresponding process in the foregoing method embodiments, and details are not described herein again.

In the several embodiments provided in this application, it should be understood that the disclosed system, apparatus, and method may be implemented in other manners. For example, the described apparatus embodiment is merely an example. For example, the unit division is merely logical function division and may be other division in actual implementation. For example, a plurality of units or components may be combined or integrated into another system, or some features may be ignored or not performed. In addition, the displayed or discussed mutual couplings or direct couplings or communication connections may be implemented by using some interfaces. The indirect couplings or communication connections between the apparatuses or units may be implemented in electronic, mechanical, or other forms.

The units described as separate parts may or may not be physically separate, and parts displayed as units may or may not be physical units, may be located in one position, or may be distributed on a plurality of network units. Some or all of the units may be selected according to actual requirements to achieve the objectives of the solutions of the embodiments.

In addition, functional units in the embodiments of this application may be integrated into one processing unit, or each of the units may exist alone physically, or at least two units are integrated into one unit.

When the functions are implemented in the form of a software functional unit and sold or used as an independent product, the functions may be stored in a computer-readable storage medium. Based on such an understanding, the technical solutions of this application essentially, or the part contributing to the prior art, or some of the technical solutions may be implemented in a form of a software product. The software product is stored in a storage medium, and includes several instructions for instructing a computer device (which may be a personal computer, a server, or a network device) to perform all or some of the steps of the methods described in the embodiments of this application. The foregoing storage medium includes: any medium that can store program code, such as a USB flash drive, a removable hard disk, a read-only memory (Read-Only Memory, ROM), a random access memory (Random Access Memory, RAM), a magnetic disk, or an optical disc.

The foregoing descriptions are merely specific implementations of this application, but are not intended to limit the protection scope of this application. Any variation or replacement readily figured out by a person skilled in the art within the technical scope disclosed in this application shall fall within the protection scope of this application. Therefore, the protection scope of this application shall be subject to the protection scope of the claims.

What is claimed is:

1. A resource allocation method for gene analysis, comprising:
    obtaining a coverage depth value of a locus in a target chromosome region according to a quantity value of sequenced reads that cover the locus in the target chromosome region;
    determining a gap in the target chromosome region according to the coverage depth value of the locus in the target chromosome region, to obtain at least two segments in the target chromosome region that use the gap as an interval, wherein the coverage depth value of the locus in the gap is less than a first threshold, the gap is a segment or a locus in the target chromosome region, and the at least two segments in the target chromosome region do not comprise the gap;
    determining one or more segments of the at least two segments in the target chromosome region as a target segment;
    obtaining a parameter value that is of the target chromosome region and that is used for resource allocation according to the target segment; and
    allocating, according to the parameter value that is of the target chromosome region and that is used for resource allocation, a computing resource to an operation in a cleansing and variant calling task that is in the gene analysis and that is performed on the sequenced reads in the target chromosome region.

2. The method according to claim 1, wherein the parameter value that is of the target chromosome region and that is used for resource allocation comprises:
    at least one of a quantity of sequenced reads in the target chromosome region or an average coverage depth of loci in the target chromosome region.

3. The method according to claim 1,
    wherein obtaining the parameter value that is of the target chromosome region and that is used for resource allocation according to the target segment comprises:
    using at least one of a quantity of the target segment, a length of the target segment, a quantity of sequenced reads in the target segment, or a coverage depth of the target segment as the parameter value that is of the target chromosome region and that is used for resource allocation, wherein the coverage depth of the target segment is an average coverage depth of loci in the target segment.

4. The method according to claim 1,
    wherein there are at least two target segments; and
    wherein obtaining the parameter value that is of the target chromosome region and that is used for resource allocation according to the target segment comprises:
    using a weighted average value of coverage depth values of the at least two target segments as the parameter value that is of the target chromosome region and that is used for resource allocation, wherein a coverage depth of the at least two target segments is an average coverage depth of loci in the at least two target segments.

5. The method according to claim 4, wherein the obtaining a parameter value that is of the target chromosome region and that is used for resource allocation according to the target segment comprises:
    calculating the weighted average value of the coverage depth values of the at least two target segments using a ratio of a length value of a target segment of the at least two target segments to a length value of the target chromosome region as a weight value of a coverage depth value of the target segment of the at least two target segments.

6. The method according to claim 4, wherein the allocating, according to the parameter value that is of the target chromosome region and that is used for resource allocation, a computing resource to an operation in a cleansing and variant calling task that is in the gene analysis and that is performed on the sequenced read in the target chromosome region comprises:
    obtaining an average value of respective parameter values that are of at least two chromosome regions and that are used for resource allocation;
    obtaining, according to the parameter value that is of the target chromosome region and that is used for resource allocation and the average value of the respective parameter values that are of the at least two chromosome regions and that are used for resource allocation, a deviation of the parameter value that is of the target chromosome region and that is used for resource allocation from the average value of the respective parameter values that are of the at least two chromosome regions and that are used for resource allocation; and
    allocating the computing resource to the operation according to the deviation.

7. The method according to claim 6, wherein the at least two chromosome regions comprise the target chromosome region.

8. The method according to claim 6, wherein the deviation comprises:
    a ratio of the weighted average value of the coverage depth values of the at least two target segments to a weighted average value of respective coverage depth values of the at least two chromosome regions; and a coverage depth of a chromosome region comprises a weighted average value of respective coverage depth values of loci in at least two segments in the chromosome region, or comprises an average coverage depth of loci in the chromosome region.

9. The method according to claim 6, wherein the deviation comprises:
    a ratio of the quantity value of the sequenced reads in the target chromosome region to an arithmetic average value of respective quantity values of sequenced reads in the at least two chromosome regions.

10. The method according to claim 6, wherein the allocating the computing resource to the operation according to the deviation comprises:

adjusting, according to the deviation, an initial computing resource used for implementing the operation, to obtain the computing resource.

11. The method according to claim 1, wherein the determining one or more segments of the at least two segments in the target chromosome region as a target segment comprises:

using, as the target segment, at least one segment that is in the at least two segments in the target chromosome region and in which a quantity of sequenced reads meets a preset quantity requirement, or a segment that is in the at least two segments in the target chromosome region and in which an average coverage depth of loci meets a preset coverage depth requirement.

12. A resource allocation apparatus for gene analysis, comprising:

at least one processor; and a non-transitory computer-readable storage medium coupled to the at least one processor and storing programming instructions for execution by the at least one processor, the programming instructions instruct the at least one processor to:

obtain a coverage depth value of a locus in a target chromosome region according to a quantity value of sequenced reads that cover the locus in a target chromosome region;

determine a gap in the target chromosome region according to the coverage depth value of the locus in the target chromosome region, to obtain at least two segments in the target chromosome region that use the gap as an interval, wherein the coverage depth value of the locus in the gap is less than a first threshold, the gap is a segment or a locus in the target chromosome region, and the at least two segments in the target chromosome region do not comprise the gap;

determine one or more segments of the at least two segments in the target chromosome region as a target segment;

determine a parameter value that is of the target chromosome region and that is used for resource allocation according to the target segment; and allocate, according to the parameter value that is of the target chromosome region and that is used for resource allocation, a computing resource to an operation in a cleansing and variant calling task that is in the gene analysis and that is performed on the sequenced reads in the target chromosome region.

13. The apparatus according to claim 12, wherein the parameter value that is of the target chromosome region and that is used for resource allocation comprises:

at least one of a quantity of sequenced reads in the target chromosome region or an average coverage depth of loci in the target chromosome region.

14. The apparatus according to claim 12,
wherein obtaining the parameter value that is of the target chromosome region and that is used for resource allocation according to the target segment comprises:

use at least one of a quantity of the target segment, a length of the target segment, a quantity of sequenced reads in the target segment, or a coverage depth of the target segment as the parameter value that is of the target chromosome region and that is used for resource allocation, wherein the coverage depth of the target segment is an average coverage depth of loci in the target segment.

15. The apparatus according to claim 12,
wherein there are at least two target segments; and
wherein obtaining the parameter value that is of the target chromosome region and that is used for resource allocation according to the target segment comprises:

use a weighted average value of coverage depth values of the at least two target segments as the parameter value that is of the target chromosome region and that is used for resource allocation, wherein a coverage depth of the at least two target segments is an average coverage depth of loci in the at least two target segments.

16. The apparatus according to claim 15, wherein the programming instructions instruct the at least one processor to:

calculate the weighted average value of the coverage depth values of the at least two target segments using a ratio of a length value of a target segment of the at least two target segments to a length value of the target chromosome region as a weight value of a coverage depth value of the target segment of the at least two target segments.

17. The apparatus according to claim 15, wherein the programming instructions instruct the at least one processor to:

obtain an average value of respective parameter values that are of at least two chromosome regions and that are used for resource allocation;

obtain, according to the parameter value that is of the target chromosome region and that is used for resource allocation and the average value of the respective parameter values that are of the at least two chromosome regions and that are used for resource allocation, a deviation of the parameter value that is of the target chromosome region and that is used for resource allocation from the average value of the respective parameter values that are of the at least two chromosome regions and that are used for resource allocation; and allocate the computing resource to the operation according to the deviation.

18. The apparatus according to claim 17, wherein the at least two chromosome regions comprise the target chromosome region.

19. The apparatus according to claim 17, wherein the deviation comprises:

a ratio of the weighted average value of the coverage depth values of the at least two target segments to a weighted average value of respective coverage depth values of the at least two chromosome regions; and a coverage depth of a chromosome region comprises a weighted average value of respective coverage depth values of loci in at least two segments in the chromosome region, or comprises an average coverage depth of loci in the chromosome region.

20. The apparatus according to claim 17, wherein the deviation comprises:

a ratio of the quantity value of the sequenced reads in the target chromosome region to an arithmetic average value of respective quantity values of sequenced reads in the at least two chromosome regions.

21. The apparatus according to claim 17, wherein the programming instructions instruct the at least one processor to:

adjust, according to the deviation, an initial computing resource used for implementing the operation, to obtain the computing resource.

22. The apparatus according to claim 12, wherein the programming instructions instruct the at least one processor to:

use, as the target segment, at least one segment that is in the at least two segments in the target chromosome region and in which a quantity of sequenced reads meets a preset quantity requirement, or a segment that is in the at least two segments in the target chromosome region and in which an average coverage depth of loci meets a preset coverage depth requirement.

* * * * *